United States Patent [19]

Parker

[11] Patent Number: 4,946,969
[45] Date of Patent: Aug. 7, 1990

[54] PROCESS OF PREPARING GAMMA-TERPINENE DIADDUCTS

[75] Inventor: David W. Parker, Holland, Pa.

[73] Assignee: Union Camp Corporation, Wayne, N.J.

[21] Appl. No.: 266,979

[22] Filed: Nov. 4, 1988

[51] Int. Cl.$^5$ ............................................. C07D 407/04
[52] U.S. Cl. ..................................... 549/237; 549/233
[58] Field of Search ................................ 549/233, 237

[56] References Cited

U.S. PATENT DOCUMENTS 4,107,420  8/1978  Schlueng et al. .................. 526/237

*Primary Examiner*—Richard L. Raymond
*Attorney, Agent, or Firm*—Edward J. Sites

[57] ABSTRACT

Diadducts of gamma-terpinene and Diels-Alder dienophiles are prepared in high yield by contacting dienophile and gamma-terpinene in a preferred molar ratio of at least about 2:1 at elevated temperatures. The resulting reaction product generally comprises at least about 80% diadducts and no more than about 20% monoadducts. Preferred dienophiles include maleic anhydride.

11 Claims, No Drawings

PROCESS OF PREPARING GAMMA-TERPINENE DIADDUCTS

BACKGROUND OF THE INVENTION

This invention relates to the preparation of Diels-Alder dienophile diadducts of gamma-terpinene, and more specifically, to the high yield preparation of maleic anhydride diadducts of gamma-terpinene.

It is well known that Diels-Alder dienophile monoadducts of terpenes, which are here defined as molecules which result upon covalent joining of one molecule of a Diels-Alder dienophile and one molecule of a terpene, can form upon contact of Diels-Alder dienophiles and terpenes at elevated temperatures. Minor amounts of diadducts, which are here defined as molecules in which there is a covalent joining between two molecules of a Diels-Alder dienophile and one molecule of terpene, can also form upon contact of Diels-Alder dienophiles and terpenes at elevated temperatures. For example, U.S. Pat. No. 1,993,031, issued to Peterson, discloses that an amorphous resinous compound may be produced by reacting maleic anhydride, a typical Diels-Alder dienophile, with a terpene cut comprising terpenes having a non-conjugated system of double bonds. Such terpenes are disclosed as being alpha-pinene, beta-pinene, terpinolene, and d-, l- and d,l-limonene. All of these terpene isomers are readily available by the distillation of turpentine or orange oil, and it is now known in the art that their reaction with maleic anhydride gives a product in which the major component is monoadduct. Gamma-terpinene comprises a minimal portion of turpentine and is not cited in the bulk of this literature.

Despite a wealth of literature relating to the reactions between terpenes and maleic anhydride, there has long been a need for a process by which substantial yields of maleic anhydride diadducts of terpenes could be obtained. High yield methods for preparing such diadducts are especially desirable, since the process of separating undesirable monoadducts from diadducts is costly and time-consuming. In an attempt to provide such a process, Schluenz et al, in U.S. Pat. No. 4,107,420, proposed reacting a non-conjugated terpene and maleic anhydride, preferably in equimolar amounts, at temperatures between 140° C. and 200° C. in the presence of 0.002 to 0.03% iodine, based on the weight of the terpene. Schluenz et al claimed that by using this process they could prepare a mixture containing more than 15% diadducts; their examples show the preparation of reaction products containing up to 45% diadduct. Terpenes disclosed as being useful in the Schluenz et al process include limonene, terpinolene, terpineol, 1,8-cineole, 1,4-cineole, and gamma-terpinene (1,4-paramenthadiene). However, gamma-terpinene is not actually utilized in any of the provided examples. Nor do they claim their process produces a specific diadduct, for example, the diadduct of gamma-terpinene. Rather their process produces a complex mixture of isomeric diadducts.

Although Schluenz et al disclose and claim the use of iodine in their process, Example 4 in their patent illustrates the process run in the absence of iodine using terpinolene as the terpene. The resulting reaction product comprises about 45% of diadduct, a yield essentially the same as that obtained in the presence of iodine. However, the product obtained in the absence of iodine is dark yellow in color rather than pale yellow. The Schluenz process, then, apparently improves the color of the product but not the yield of diadduct.

U.S. Pat. No. 4,670,504 to Cardenas discloses a tackifier composition formed from a resin which is preferably a polymerized terpene that subsequent to formation is reacted with an acid or anhydride such as maleic anhydride. It is disclosed that gamma-terpinene is one of many possible terpenes which can be used to prepare the polyterpene. The anhydride is said to become chemically incorporated with the polyterpene in a manner which does not appear to be fully understood. The addition of maleic anhydride to a pre-existing terpene polymer is to be distinguished from the present invention in which maleic anhydride is added to terpene monomer.

Diels-Alder dienophile diadducts of gamma-terpinene are expected to find extensive commerical use. For example, maleic anhydride diadducts will likely be employed in alkyd formulations and as curing agents for epoxies and the like. Adduction between maleimides or bismaleimides and gamma-terpinene may lead to novel polyimides and/or their precursors. The product polyimides are expected to be useful composite components for high temperature structural applications. So called "mixed" Diels-Alder dienophile diadducts of gamma-terpinene, in which one molecule of gamma-terpinene is covalently joined with one mole each of two different Diels-Alder dienophiles, such as maleic anhydride and acrylic acid, are expected to be useful as well.

Therefore, it is an object of this invention to provide diadducts of gamma-terpinene and maleic anhydride, maleimides, and acrylates, respectively.

It is another object of this invention to provide "mixed" diadducts of gamma-terpinene.

It is a further object of this invention to provide diadducts of gamma-terpinene and various Diels-Alder dienophiles.

It is still another object of this invention to provide diadducts of gamma-terpinene and various Diels-Alder dienophiles without appreciable formation of monoadducts.

It is yet another object of this invention to provide diadducts of gamma-terpinene and various Diels-Alder dienophiles in a more economically desirable manner than previously known methods.

SUMMARY OF THE INVENTION

It has now been found that gamma-terpinene cleanly and readily reacts with Diels-Alder dienophiles to give a diadduct in high yield, i.e., in major proportion and commonly 80% or more. By contacting dienophiles and qamma-terpinene, preferably in molar ratios of about 2:1, at temperatures in the range of about 140° to 200° C., a reaction product is obtained which can comprise at least about 80% diadduct and generally no more than about 20% monoadduct. Gamma-terpinene presently appears to be unique among terpene molecules in that no other material has been found to yield such high proportions of diadduct. Unlike the prior art process disclosed in Schluenz et al, the process of this invention is run in the absence of iodine. The resulting crude reaction product is a pale yellow solid and does not suffer from high coloration.

The gamma-terpinene/maleic anhydride diadducts of this invention are useful, for example, as curing agents for epoxies and the like. Prior art reaction products containing predominately monoadduct are inferior for use as alkyd components and curing agents since the monoadducts act as reaction chain-stoppers rather than as cross-linking agents and thus, for example, lead to cured epoxy materials with relatively low heat distortion temperatures. In order for such high monoadduct-containing products to provide optimum properties, they must first be subjected to costly and time-consuming purification steps to separate out the desired diadducts. By contrast, the reaction products of this invention, by virtue of their high diadduct content, may be more easily purified or may even be used directly as cross-linking or curing agents for alkyd or epoxy resin systems.

The term "terpene" covers a wide variety of compounds containing ten carbon atoms, some of which are cyclic and unsaturated. Among the latter are a group called menthadienes, which are monocyclic $C_{10}H_{16}$ hydrocarbons having their carbon atoms arranged as in p-isopropyl toluene and limonene. The terpene compound from which the diadducts of this invention are prepared is gamma-terpinene, also referred to as 1,4-paramenthadiene, a non-conjugated diene having formula 1. Gamma-terpinene is not found in appreciable amounts in turpentine but is instead a product of the acid catalyzed isomerization of turpentine. It is obtained after such an isomerization process by careful fractional distillation of the isomerizate.

In preferred embodiments of this invention, gamma-terpinene is contacted with a Diels-Alder dienophile at a temperature within the range of about 50° to 200° C., preferably about 155° to 170° C. Representative Diels-Alder dienophiles include maleic anhydride, maleimides, acrylonitrile, acrylic acid, methyl acrylate, and various chemical moieties, including acrylic acid derivatives. Maleic anhydride is particularly preferred. As will be appreciated by one of skill in the art, a wide variety of Diels-Alder dienophiles (which are known per se) may advantageously be employed. The order of addition of the dienophile and gamma-terpinene is not believed to be critical to the practice of this invention. For best results, it is desired that the reactants comprise at least about two moles of dienophile for each mole of gamma-terpinene.

The lowest temperature at which the reaction will spontaneously occur is about 155° C. with the preferred temperature range beginning at about 160° C. The upper limit of the temperature range is generally determined by the boiling points of the reactants, generally about 170° at 1 atmosphere of pressure. At temperatures above about 165° C., the diadduction between gamma-terpinene and, for example, maleic anhydride occurs immediately upon contacting the reactants. It is best not to permit the temperature to fall substantially below about 155° C. because, in the case where terpene is being added to maleic anhydride, unreacted terpene tends to accumulate, allowing for a very exothermic reaction once sufficient heat is provided to begin rapid reaction.

The reaction is preferably run without solvent, but solvents such as aliphatic or aromatic hydrocarbons, esters or ethers can be used, so long as it is both inert with respect to the adduction reaction and has a boiling point greater than about the reaction temperature. Representative inert organic solvents include p-cymene (a common terpene impurity of gamma-terpinene), 2-methoxyethyl ether, and other polyethers. It is preferred that the gamma-terpinene feedstocks be of good purity, at least about 75%, as any olefinic terpene impurities react to give mainly undesirable monoadducts.

It is believed that when gamma-terpinene and, for example, maleic anhydride are combined, an initial "Ene" reaction occurs resulting in the covalent joining of one terpene and one maleic anhydride unit and a shift of one double bond so that a conjugated system of double bonds results. These conjugated double bonds are then believed to immediately undergo a Diels-Alder reaction with additional maleic anhydride at the temperature required for the Ene reaction. The product is found to be a terpene twice adducted with maleic anhydride. This Ene/Diels-Alder addition is presently believed to be unique to gamma-terpinene among paramenthadienes. This reaction sequence is shown in the schematic, wherein the addition of the first mole of maleic anhydride is shown in brackets and then the products obtained upon the addition of the second mole of maleic anhydride are set forth as formulas 2, 3, 4, and 5.

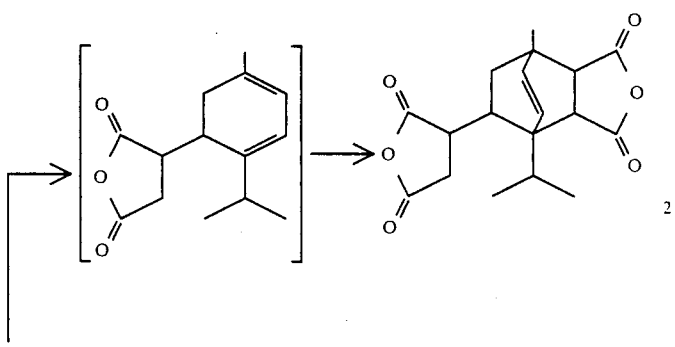

-continued

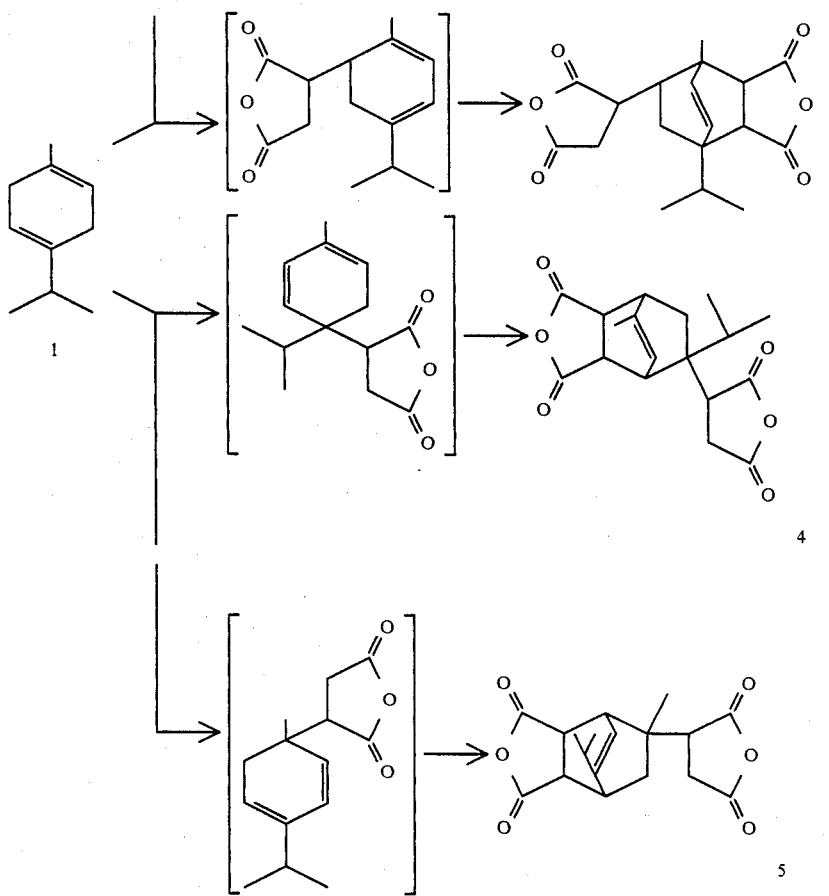

Unlike the prior art Schluenz et al process described in U.S. Pat. No. 4,107,420, the process of this invention is carried out without the addition of iodine. Contrary to what would have been expected in view of the disclosure of the Schluenz et al patent, distinctly different products are obtained in the absence of iodine and in the presence of iodine. The diadduct yield of the process of this invention is almost twice as much as the yield of any of the Schluenz et al diadducts. The reaction product of the process of this invention consists largely of only about 4 isomers (represented by formulas 2–5) and also generally has light color; measured on the Gardner scale, the color of this reaction product is typically about 1.

The invention will now be described, and further compared to the Schluenz et al process, in the following examples wherein parts and percents are by weight and temperatures are in degrees Celsius unless otherwise indicated.

EXAMPLE 1

A reaction flask was set up with necks fitted with a mechanical stirrer, an addition funnel, temperature probe, and a reflux condenser topped with a nitrogen inlet which maintained in inert atmosphere in the reaction flask. To the reaction flask containing 104g of maleic anhydride at 155° was added 75g of gamma-terpinene having 98% purity. The addition took 25 minutes and the temperature fluctuated between 153° and 165°. Upon cooling, the product mixture was Kugelrohr distilled to remove unreacted terpene, maleic anhydride and monoadducts. The purified product was obtained in 87% yield based on total charge of reactable monomers. The product contains about 95% diadduct and 5% monoadduct as judged by gel permeation chromatography using a refractive index detector. The product has a neat Gardner color of 2, and a 50% by weight solution in tetrahydrofuran has a Gardner color of 1. The product will occasionally have a yellow or red tint. The ring-and-ball softening point of the product was 97° C.

COMPARATIVE EXAMPLE 1

The same general process taught by Schluenz et al in U.S. Pat. No. 4,107,420 for preparing terpene/maleic anhydride diadduct was repeated using 98% pure gamma-terpinene. Using the same apparatus as described in Example 1, the flask was charged with 98.2g maleic anhydride (1 mole) and heated to a temperature of 175° C. A crystal of iodine weighing 0.03g was added, and then 136g (1 mole) of gamma-terpinene was dripped in slowly. After addition was complete, a sample analyzed by gel permeation chromatography indicated that a diadduct was present only in 9% yield, monoadduct was present in 87% yield. Unreacted terpenes constituted 4% of the product mixture.

The procedure was repeated using maleic anhydride which was dried by azeotropic distillation from toluene/maleic anhydride; a similar product distribution was obtained.

COMPARATIVE EXAMPLE 2

The procedure of Schluenz et al was repeated except no iodine was used. A product mixture consisting of 60% diadduct, 23% monoadduct and 18% unreacted terpenes was obtained. This represents a molar yield of diadduct of over 84% based on available maleic anhydride.

What is claimed is:

1. A method for preparing diadducts of a Diels-Alder dienophile and gamma-terpinene which comprises heating in the absence of iodine a mixture of gamma-terpinene and about two molar equivalents of the Diels-Alder dienophile based upon the moles of gamma-terpinene at a temperature between about 155° C. and the boiling point of the mixture for a time sufficient to react substantially all of the gamma-terpinene.

2. A method for preparing diadducts of a Diels-Alder dienophile and gamma-terpinene which comprises heating one molar equivalent of gamma-terpinene in the absence of iodine to a temperature at which gamma-terpinene will undergo an "Ene" reaction with the Diels-Alder dienophile, adding about two molar equivalents of the Diels-Alder dienophile, and maintaining the temperature until substantially all of the gamma-terpinene has reacted.

3. A method for preparing diadducts of a Diels-Alder dienophile and gamma-terpinene which comprises heating in the absence of iodine two molar equivalents of the Diels-alder dienophile to a temperature sufficient for the Diels-Alder dienophile to undergo an "Ene" reaction with gamma-terpinene, adding one equivalent of gamma-terpinene and maintaining the temperature until substantially all of the gamma-terpinene has reacted.

4. The method of claim 1 wherein the Diels-Alder dienophile is maleic anhydride and the temperature is between about 155° C. and about 170° C.

5. The method according to claim 1 wherein the Diels-Alder dienophile is maleic anhydride.

6. The method according to claim 3 wherein the Diels-Alder dienophile is maleic anhydride.

7. The method of claim 1 wherein said mixture further comprises an inert organic solvent having a boiling point greater than about 160° C. at 1 atmosphere pressure.

8. The method of claim 1 wherein to said gamma-terpinene is added a part of a blend of terpenes and comprises at least about 75 mole percent of the total amount of terpenes present in said blend.

9. The method of claim 4 further comprising recovering, in admixture, compounds of the formulas

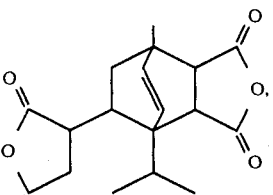

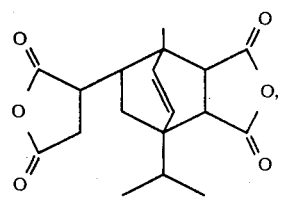

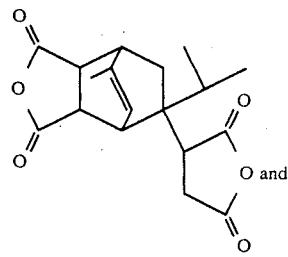

O and

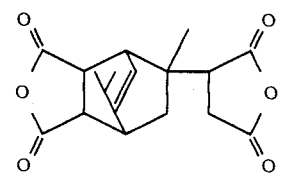

from the reaction mixture.

10. The method of claim 1 wherein said diadducts are formed in major proportion from the reaction.

11. The method of claim 1 wherein said diadducts comprise at least about 80% by weight of the reacted mixture.

* * * * *